United States Patent [19]

Masuhara et al.

[11] Patent Number: 5,183,403
[45] Date of Patent: Feb. 2, 1993

[54] PROCESS FOR ADHESION OF ORTHODONTIC BRACKET

[75] Inventors: Eiichi Masuhara, Tokyo; Shigeo Komiya, Urawa, both of Japan

[73] Assignee: Japan Institute of Advanced Dentistry, Tokyo, Japan

[21] Appl. No.: 718,397

[22] Filed: Jun. 20, 1991

[51] Int. Cl.⁵ .............................................. A61C 3/00
[52] U.S. Cl. ............................................ 433/9; 433/8
[58] Field of Search ....................... 433/8, 9; 206/63.5

[56] References Cited

U.S. PATENT DOCUMENTS

| | | | |
|---|---|---|---|
| 3,745,653 | 7/1973 | Cohl | 433/9 |
| 4,063,360 | 12/1977 | Waller | 433/9 |
| 4,749,352 | 6/1988 | Nicholson | 433/9 |
| 4,952,142 | 8/1990 | Nicholson | 433/9 |
| 4,978,007 | 12/1990 | Jacobs et al. | 206/469 |
| 4,979,611 | 12/1990 | Bolliger et al. | 206/83 |
| 5,078,596 | 1/1992 | Carberry et al. | 433/8 |

*Primary Examiner*—Robert P. Swiatek
*Assistant Examiner*—Cindy A. Cherichetti
*Attorney, Agent, or Firm*—Nixon & Vanderhye

[57] ABSTRACT

Disclosed herein are an orthodontic bracket which comprises a photopolymerization-type adhesive layered and fixed on a back surface portion of a bracket main body made of a light-transmitting material, a kit which comprises the bracket hermetically sealed in a light-shielding container, and a process for the adhesion of the bracket.

1 Claim, 2 Drawing Sheets

PROCESS FOR ADHESION OF ORTHODONTIC BRACKET

This is a continuation of PCT application No. PCT/JP89/01109 filed Oct. 27, 1989.

DESCRIPTION

1. Technical Field

The present invention relates to an orthodontic bracket made of a light-transmitting material, and more particularly to an orthodontic bracket comprising a photo-polymerization-type adhesive layered and fixed on a back surface portion of a bracket main body, a kit comprising the bracket, and a process for the adhesion of the bracket.

2. Background Art

In the field of orthodontics, a direct bonding system is widely used in which an orthodontic bracket is adhered directly to a tooth surface with a resin adhesive.

The brackets used in the system have been changed from that of metal to of plastic, ceramic, composite and the like which have a more aesthetic appearance.

These conventional brackets were adhered to the tooth surface by means of an adhesive which had been separately prepared. Namely, in a medical practice, it has been a common practice to separately prepare a cold-setting-type adhesive paste beforehand, to apply the adhesive paste to both the back surface portion of the bracket main body and the tooth surface and to fix the bracket main body in a proper position under pressure, or to use a powder-liquid-type adhesive with a brush-on technique.

In these methods, however, the adhesion process is complicated and requires a long time. In addition, a high degree of skill is required for carrying out these methods. Consequently, if the methods are not skillfully performed, the timing of the adhesion will be very likely lost due to the progress of a setting reaction of the adhesive. In such situations, there has often occurred a failure in placement of the bracket in the proper position or a failure to develop satisfactory, adhesive strength, resulting in a clinical failure of the orthodontic practice.

DISCLOSURE OF INVENTION

Accordingly, in an aspect of the present invention, there is provided the orthodontic bracket which comprises the photopolymerization-type adhesive layered and fixed on the back surface portion of the bracket main body made of a the light-transmitting material.

The light-transmitting material for use as a material for the bracket main body in the present invention includes, for instance, a thermoplastic resin such as polycarbonate, polymethyl methacrylate and polyether-sulfone, a composite resin obtained by blending an organic filler into a thermoplastic resin, a composite resin comprising a multifunctional methacrylate and a silica filler, and ceramic comprising zirconia or alumina.

The photopolymerization-type adhesive for use in the present invention may be a liquid mixture of a polymerizable monomer containing a combination of a photochemical sensitizer and a reducing agent or a combination of a photochemical sensitizer and an organic peroxide. It is preferable to incorporate known inorganic or organic fillers into the photopolymerization-type adhesive, in order to prepare the adhesive in a pasty form with an enhanced consistency which can facilitate the layering and fixation of the adhesive onto the back surface portion of the bracket main body.

The photochemical sensitizer may be, for instance, camphor quinone or a derivative thereof, benzil or thiopyrylium.

The reducing agent may be, for example, a tertiary amine such as N,N-dimethyl-p-toluidine and tri-n-butylamine, a sulfinic acid (salt), an aralkylbarbituric acid or an acid anydride.

The organic peroxide may be, for instance, benzoyl peroxide, lauroyl peroxide, benzophenone peroxide, t-butyl peroxide, t-butyl peroxybenzoate, or 2,5-dimethyl-2,5-di(benzoylperoxy)hexane.

Typical examples of the polymerizable monomer include, particularly, methacrylic acid esters and acrylic acid esters.

As monomethacrylate, there may be mentioned methyl methacrylate, ethyl methacrylate, butyl methacrylate, cyclomethacrylate, benzyl methacrylate, 2-hydroxyethyl methacrylate, 4-methacryloxyethyltrimellitic anhydride, 4-methacryloxyethyltrimellitic acid and methacryloxyethyl phthalate.

As dimethacrylate, there may be mentioned ethylene glycol dimethacrylate, diethylene glycol dimethacrylate, bisphenol A dimethacrylate, triethylene glycol dimethacrylate, tetraethylene glycol dimethacrylate, 2,2-bis(p-2'-hydroxy-3'-methacryloxypropoxyphenyl)-propane, di(methacryloxyethyl)trimethylhexamethylenediurethane, 2,2-bis(4-methacryloxypolyethoxyphenyl)propane and 4,8-di(methacryloxymethylene)-tricyclo[5,2,1,0$^{2,6}$]decane.

As monoacrylate, there may be mentioned methyl acrylate, ethyl acrylate, butyl acrylate, cyclohexyl acrylate and benzyl acrylate.

As diacrylate, there may be mentioned ethylene glycol diacrylate, diethylene glycol diacrylate, triethylene glycol diacrylate and tetraethylene glycol diacrylate.

In the present invention, other known polymerizable monomers than the above-mentioned ones may also be used, naturally.

As the filler in the photopolymerization-type adhesive, known inorganic or organic fillers may be used. Namely, ceramic powders such as silica powder, glass powder, quartz powder and alumina, and plastic powders such as polymethyl methacrylate particulates may be used. Materials obtained by treating the surfaces of the above powders with a silane coupling agent may also be preferably used as the filler.

The contents of each constituent in the photopolymerization-type adhesive of the present invention can be determined appropriately by those skilled in the art. For instance, preferably, the present adhesive comprises 60 to 99 parts by weight of the polymerizable monomer, 0.01 to 1 part by weight of the photochemical sensitizer, 0.01 to 1 part by weight of the reducing agent or 0.01 to 1 part by weight of the organic peroxide, and 1 to 40 parts by weight of the filler.

In another aspect of the present invention, there is provided the orthodontic bracket kit which comprises the above-mentioned orthodontic bracket hermetically sealed in a light-shielding container.

In the kit, preferably, a plurality of the orthodontic brackets according to the present invention are separately and independently contained and sealed.

Because the photopolymerization-type adhesive is layered and fixed on the back surface of the bracket main body of the orthodontic bracket according to the present invention, the bracket should be maintained in the light-shielding container over a storage period before use, so as to prevent the exposure of the bracket from the exposure to light. The light-shielding container may be a container which comprises a main body made of polyolefin such as polypropylene and polyethylene, Teflon, polyacetal, polyester, silicone or metal, for instance or black polypropylene, and a sealant made of an aluminum foil, an aluminum laminate film, a stainless steel foil or the like.

In a further aspect of the present invention, there is provided a process for the adhesion of the above-mentioned orthodontic bracket, comprising pressing the bracket against the tooth surface pretreated with an acid, and irradiating the bracket with light.

The irradiation with light may be carried out by use of a commercially available visible light emitter, and an irradiation time of about 5 to 10 seconds suffices.

In order to enhance the degree of the adhesion of the orthodontic bracket of the present invention to the tooth surface, it is preferable to preliminarily subject the tooth surface to an acid treatment such as phosphoric acid etching and then to apply to liner to the tooth surface, followed by pressing the bracket against the tooth surface.

The liner may be any of the liners which are ordinarily used in the dental field, a liner which contains as a catalyst in addition to the polymerizable monomer an organic peroxide, a combination of an photochemical sensitizer with an organic peroxide, or a combination of a photochemical sensitizer with a reducing agent, being particularly preferable.

As the polymerizable monomer, the photochemical sensitizer, there may be used the reducing agent and the organic peroxide, those used for the above-mentioned photopolymerization-type adhesive.

The mixing ratios of each constituent of the liner may be appropriately determined by those skilled in the art, in the same manner as in the case of the photopolymerization-type adhesive.

Some embodiments of the light-shielding container in which the orthodontic bracket of the present invention is hermetically sealed will now be described below while referring to the drawings.

BEST MODE FOR CARRYING OUT THE INVENTION

Figure 1:
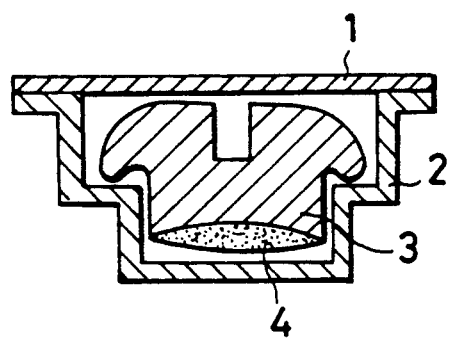
FIG. 1 shows a sectional view of an orthodontic bracket 3 of the present invention contained in a light-shielding polyolefin container (black-colored) 2, in which a photopolymerization-type adhesive 4 is layered and fixed on a back surface portion of the bracket 3, and the polypropylene container 2 is hermetically sealed with a seal of an aluminum foil 1.

The present invention will now be explained in detail while referring to the Examples below.

EXAMPLE 1

A paste A, which was a photopolymerization-type adhesive, was layered on a base (back) surface of EKUSERA (trade name; a composite bracket produced by Morita Tokyo Seisakusho K.K.). The resulting bracket according to the present invention, with the adhesive 4 layered thereon, was set in a black polypropylene container 2, and the container was sealed on the upper side with a hermetic sealant of an aluminum laminate film to shield light.

| Preparation of Paste A | |
| --- | --- |
| 2,2-Bis(p-2'-hydroxy-3'-methacryl-oxypropoxyphenyl)propane | 40 parts by weight |
| Di(methacryloxyethyl)trimethyl-Hexamethylenediurethane | 20 parts by weight |
| Triethylene glycol dimethacrylate | 20 parts by weight |
| Methyl methacrylate | 20 parts by weight |
| AEROSIL R972 (trade name; a fine Silica powder produced by Nippon Aerosil Co., Ltd.) | 17 parts by weight |
| Camphorquinone | 0.4 part by weight |
| Tri-n-butylamine | 0.8 part by weight |

The materials set forth above were sufficiently kneaded to prepare the paste A.

| [Preparation of Liner B] | |
| --- | --- |
| 2,2-Bis(p-2'-hydroxy-3'-methacryl-Oxypropoxyphenyl)propane | 50 parts by weight |
| 2,2-Bis(4-methacryloxypolyethoxy-phenyl)propane | 20 parts by weight |
| Triethylene glycol dimethacrylate | 20 parts by weight |
| Ethyl methacrylate | 20 parts by weight |
| Camphorquinone | 0.4 part by weight |
| Benzoyl peroxide | 0.4 part by weight |

The materials set forth above were sufficiently mixed and agitated to prepare a liner B.

After the liner was applied to an enamel surface, the bracket of the present invention with the adhesive layered thereon was taken out of the container by means of a pair of tweezers, and pressed against the surface. Due to the presence of an appropriate amount of the adhesive preliminarily layered on the base surface of the bracket, the amount of the adhesive protruding to the surroundings of the base was smaller than the corresponding amount produced in a conventional process. After adjustment of the mounting position of the bracket, the bracket was irradiated with light for about 5 seconds by use of QUICK LIGHT (trade name; a visible light emitter, produced by Morita Seisakusho K.K.). After 10 minutes, binding with a wire was carried out, and the bracket was found to be satisfactorily adhered firmly and showed no sway. Even after 6 months, slipping of the bracket off the tooth surface was not observed.

EXAMPLE 2

PORCELAIN LINER M (trade name; a silane coupling agent, produced by Sun Medical Co., Ltd.) was applied to the base surface of TORAYCERAM (trade name; a ceramic bracket, produced by Toray Industries, Inc.), and a paste C of a photopolymerization-type adhesive was layered thereon. The resulting bracket according to the present invention with the adhesive layered thereon was set in an aluminum container for shielding light, and an upper surface of the container was sealed by a hermetic sealant of an aluminum laminate film to shield light.

[Preparation of Paste C]

| | |
|---|---|
| 2,2-Bis(p-2'-hydroxy-3'-metacryl-Oxypropoxyphenyl)propane | 40 parts by weight |
| Triethylene glycol dimethacrylate | 16 parts by weight |
| 2,2-Bis(4-methacryloxypolyethoxyphenyl)propane | 10 parts by weight |
| Methyl methacrylate | 14 parts by weight |
| AEROSIL R972 | 20 parts by weight |
| Camphorquinone | 0.5 part by weight |
| Benzoyl peroxide | 0.3 part by weight |
| Methoxyhydroquinone | 0.02 part by weight |

The materials set forth above were kneaded sufficiently to prepare the paste C.

[Preparation of Liner D]

| | |
|---|---|
| 2,2-Bis(4-methacryloxypolyethoxyphenyl)propane | 30 parts by weight |
| 2-Hydroxyethyl methacrylate | 50 parts by weight |
| Methyl methacrylate | 20 parts by weight |
| N,N-Dimethyl-p-toluidine | 0.5 part by weight |
| Camphorquinone | 0.5 part by weight |

The materials set forth above were sufficiently kneaded and agitated to prepare a liner D. After the liner was applied to an enamel surface, the bracket of the present invention with the adhesive layered thereon was taken out of the container by means of a pair of tweezers, and pressed against the surface. Due to the presence of an appropriate amount of the adhesive preliminarily layered on the base surface of the bracket, the amount of the adhesive protruding to the surroundings of the base was smaller than the corresponding amount produced in a conventional process. After adjustment of the mounting position of the bracket, the bracket was irradiated with light for 10 seconds by use of QUICK LIGHT. After 10 minutes, binding with a wire was carried out, and the bracket was found to be adhered satisfactorily and showed no sway. Even after 6 months, slipping of the bracket off the tooth surface was not observed.

COMPARATIVE EXAMPLE

A tooth surface was etched for 15 seconds in a 35% aqueous solution of phosphoric acid, washed with water and dried. The tooth surface was then coated with TRANSBOND PRIMER (trade name, an orthodontic adhesive primer of a photo setting type, produced by Unitek Japan Corp.). Next, EKUSERA coated on its back surface with TRANSBOND (trade name, a photo-setting type orthodontic adhesive, produced by Unitek Japan Corp.) was pressed against the tooth surface, and irradiated with light for 15 seconds by use of QUICK LIGHT. Though the bracket showed good adhesion, it was so difficult to apply the adhesive to the small back surface of the bracket that it was impossible to achieve an appropriate application. When the coating amount was too small, the resulting adhesive strength was unsatisfactory, whereas when the coating amount was too large, the adhesive protruded so that much time was required to remove the protruded adhesive by using an instrument.

Figure 2:
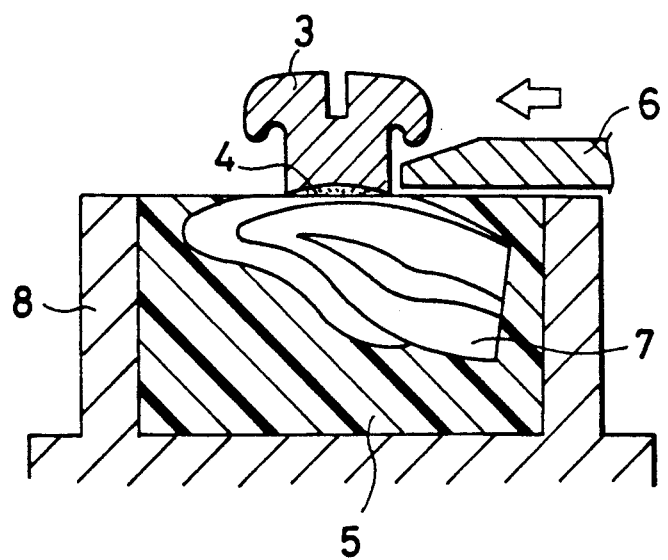
FIG. 2 illustrates a device for the measurement of adhesive strength under compressive shear.
Figure 3:
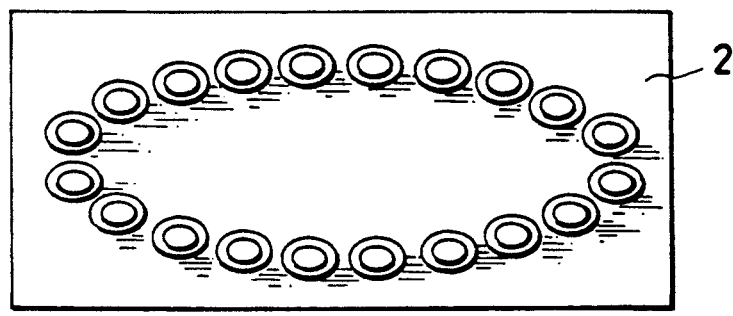
FIG. 3 shows a bottom surface of an orthodontic bracket kit according to the present invention.
Figure 4:
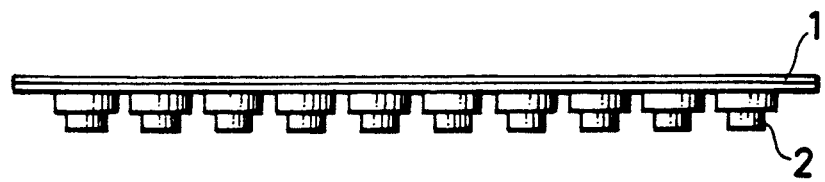
FIG. 4 shows a side surface of the orthodontic bracket kit of the present invention.

The adhesive strength under compressive shear was measured as follows. As shown in FIG. 2, a bracket 3 with a photopolymerization-type adhesive 4 preliminarily layered on a back surface thereof was pressed against an enamel surface of a bovine tooth 7 embedded in a resin 5 contained in a holder 8. In this case, the enamel surface of the bovine tooth 7 was preliminarily etched with 35% phosphoric acid, washed with water and dried. The bracket in the pressed position was irradiated with light for 10 seconds by means of the visible emitter, QUICK LIGHT. After 30 minutes, the bracket thus adhered was pressed by a shearing jig 6, and the load under which the bracket base and the enamel of the bovine tooth were released from each other was measured. The measured value was taken as the adhesive strength under compressive shear.

| | Adhesive Strength (kg) under Compressive Shear |
|---|---|
| Example 1 | 12.9 |
| Example 2 | 11.4 |
| Comparative Example | 5.6 |

INDUSTRIAL APPLICABILITY

The orthodontic bracket according to the present invention is made of the light-transmitting material, and therefore has extremely high aesthetic properties, as apparent from the comparison of clinical examples in which as conventional metallic bracket was fitted to a jaw with those in which the orthodontic bracket of the present invention was fitted to the jaw. Further, due to the presence of the photopolymerization-type adhesive preliminarily layered firmly on the back surface portion of the main body of the bracket of the present invention, it is possible to take a sufficient time for the adjustment of the bracket position in the adhesion of the bracket during the orthodontic process. Further, a desired adhesive strength can be obtained instantaneously and for a long time, simply by the short-time light irradiation an operator carries out. Therefore, even where it is required to adhere the brackets to a multiplicity of teeth in the oral cavity of a patient, it is possible to complete the entire treatment within an extremely short period of time. As a result, it is possible not only to reduce markedly the period of time during which the patient must painfully keep his mouth open, but also to enhance the efficiency of the operation for mounting the bracket.

Moreover, the kit according to the present invention, comprising the bracket of the present invention hermetically sealed in the light-shielding container, enables easy handling of the bracket and is suitable for the long-time storage. Furthermore, the kit comprising a plurality of the brackets hermetically sealed in an independent form with each other enables an effective use of the individual bracket and is, therefore, highly economical and rational.

We claim:

1. A process for adhering an orthodontic bracket made of a light-transmitting material and having a photopolymerizable adhesive layered and fixed on a back surface portion thereof, said process comprising applying a liner which is a liquid mixture of polymerizable monomer containing as a catalyst one of an organic peroxide, a combination of an organic peroxide with a photochemical sensitizer and a combination of a reducing agent with a photochemical sensitizer to a tooth surface pretreated with an acid, pressing the orthodontic bracket against the tooth surface and irradiating the bracket with light.

* * * * *